(12) United States Patent
Murphy et al.

(10) Patent No.: US 10,429,368 B2
(45) Date of Patent: Oct. 1, 2019

(54) METHOD AND DEVICE FOR DETECTING THIOCYANATE IONS IN MARINE ENVIRONMENTS

(71) Applicant: Roger Williams University, Bristol, RI (US)

(72) Inventors: Clifford Brewster Murphy, North Attleboro, MA (US); Clifford John Timpson, Little Compton, RI (US)

(73) Assignee: Roger Williams University, Bristol, RI (US)

( * ) Notice: Subject to any disclaimer, the term of this patent is extended or adjusted under 35 U.S.C. 154(b) by 71 days.

(21) Appl. No.: 15/787,867

(22) Filed: Oct. 19, 2017

(65) Prior Publication Data

US 2018/0113105 A1    Apr. 26, 2018

Related U.S. Application Data

(60) Provisional application No. 62/411,031, filed on Oct. 21, 2016.

(51) Int. Cl.
*G01N 33/18* (2006.01)
*G01N 27/48* (2006.01)

(52) U.S. Cl.
CPC ..... *G01N 33/1826* (2013.01); *G01N 33/1886* (2013.01); *G01N 27/48* (2013.01); *G01N 33/182* (2013.01)

(58) Field of Classification Search
CPC ...... G01N 27/48; G01N 33/18; G01N 33/182; G01N 33/1826; G01N 33/1886; Y10T 436/172307; Y10T 436/173076; Y10T 436/18; Y10T 436/19

USPC ........ 436/83, 109, 110, 119, 124, 125, 149, 436/150, 151, 164; 422/82.01–82.03, 422/82.05
See application file for complete search history.

(56) References Cited

U.S. PATENT DOCUMENTS

| | | | |
|---|---|---|---|
| 5,124,011 A * | 6/1992 | Rogers | G01N 27/48 205/782 |
| 6,002,817 A | 12/1999 | Kopelman et al. | |
| 8,267,883 B2 | 9/2012 | DiMauro et al. | |
| 9,607,301 B2 | 3/2017 | Gaudiana et al. | |
| 2010/0269894 A1 | 10/2010 | Misra et al. | |

(Continued)

FOREIGN PATENT DOCUMENTS

| | | |
|---|---|---|
| CN | 102008980 A | 4/2011 |
| CN | 103127958 A | 6/2013 |

OTHER PUBLICATIONS

McCabe et al. Abstracts of Papers, 251st ACS National Meeting & Exposition, San Diego, CA, US, Mar. 13-17, 2016.*

(Continued)

*Primary Examiner* — Maureen Wallenhorst
(74) *Attorney, Agent, or Firm* — Barlow, Josephs & Holmes, Ltd.

(57) ABSTRACT

The present invention provides a novel and unique device, method and system that detects thiocyanate in seawater with the halide ions present that can be provided in a hand-portable device that offers detection limits to 1-2 ppb which at least twice as sensitive as the nearest known device in the current state of the art. The sensor is also sensitive to nitrate ions (NO3−) in seawater at similar ppb concentrations as thiocyanate.

4 Claims, 6 Drawing Sheets

(56) References Cited

U.S. PATENT DOCUMENTS

2016/0356921 A1    12/2016  Shen et al.

OTHER PUBLICATIONS

Flynn et al. Abstracts, 41st Northeast Regional Meeting of the American Chemical Society, Binghamton, NY, US, Oct. 5-8, 2016.*
Sweet et al. Abstracts, 41st Northeast Regional Meeting of the American Chemical Society, Binghamton, NY, US, Oct. 5-8, 2016.*
Czolk et al., "Studies on the anion sensitivity of immobilized metalloporphyrins for application as optochemical sensors", Sensors and Actuators, 1996; B 30: 61-63.
Imahori et al., "Effects of Porphyrin Substituents and Adsorption Conditions on Photovoltaic Properties of Porphyrin-Sensitized TiO2 Cells", J. Phys. Chem. 2009 American Chemical Society; 113: 18406-18413.
Ma et al., "Recent developments in cyanide detection: A review", Analytica Chimica Acta, 2010 Elsevier; 673: 117-125.
Silva et al., "Optical fiber based methodology for assessment of thiocyanate in seawater", J. Environmental Monitoring, 2011; 13: 1811-1815.
Sun et al., "Piezoelectric quartz crystal (PQC) with photochemically deposited nano-sized Ag particles for determining cyanide at trace levels in water", Sensors and Actuators, 2005; 108: 925-932.
Zhang et al., "Colorimetric and Fluorescent Sensing of SCN-Based on meso-Tetraphenylporphyrin/meso-Tetraphenylporphyrin Cobalt (II) System", Sensors 2007; 7: 410-419.
Szpakolski et al., "Silane: A new linker for chromophores in dye-sensitised solar cells", Polyhedron, 2013; 52: 719-732.

* cited by examiner

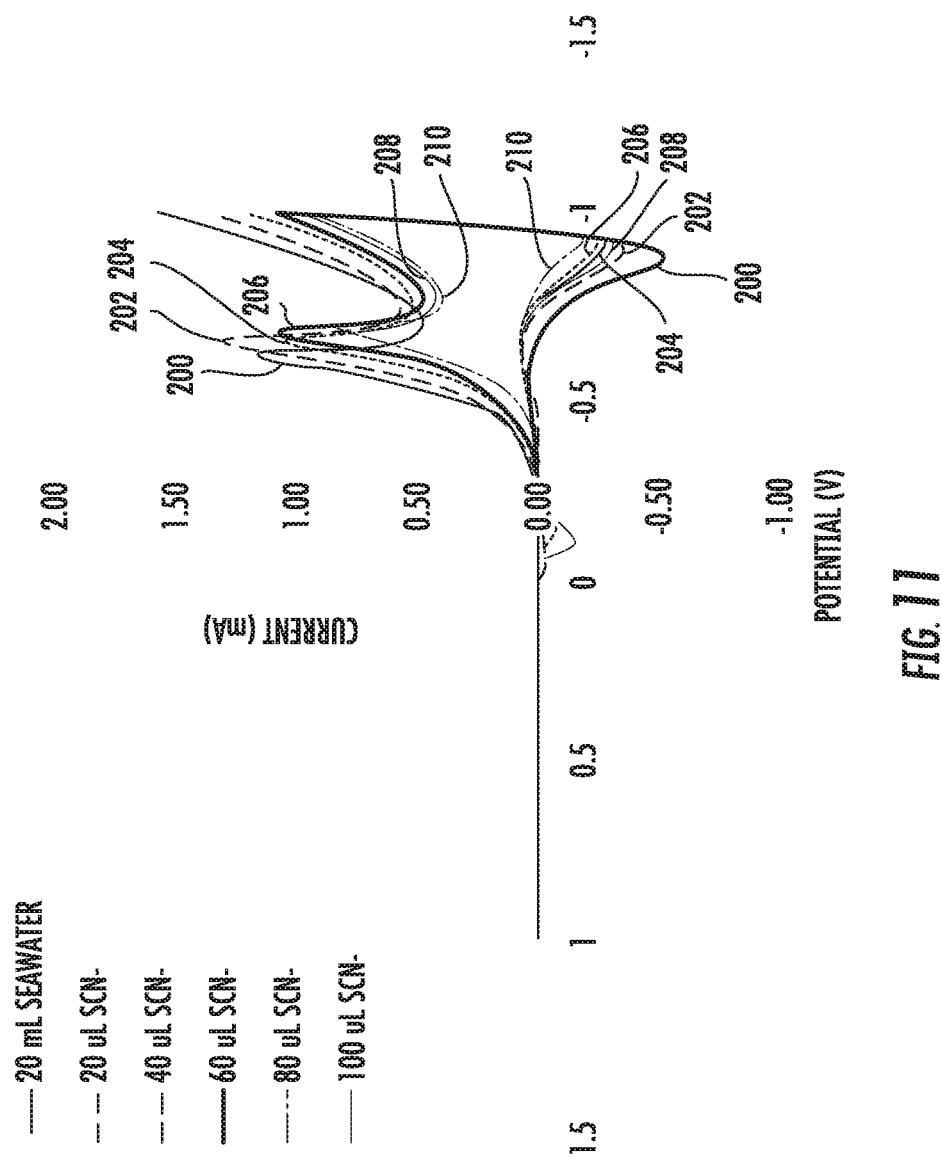

METHOD AND DEVICE FOR DETECTING THIOCYANATE IONS IN MARINE ENVIRONMENTS

CROSS REFERENCE TO RELATED APPLICATION

This patent document claims priority to earlier filed U.S. Provisional Patent Application No. 62/411,031, filed on Oct. 21, 2016, the entire contents of which are incorporated herein by reference.

GOVERNMENT SUPPORT

This invention was made with government support under RI-EPSCoR SURF grant No. 1004057, starting Aug. 1, 2015, awarded by the National Science Foundation. The government has certain rights in the invention.

BACKGROUND OF THE INVENTION

This chemosensor device has direct application in assisting law enforcement in identifying fish that have been illegally caught via the practice of cyanide fishing by detecting thiocyanate as an analyte in sea water. This would also have application in characterizing the efficacy of anti-fouling coating of boats and ships, by detecting the diffusion of thiocyanate to surrounding water. Thiocyanate is typically an additive to motor oil to prevent corrosion in off-shore drilling apparatus and in marine engines—sensitive thiocyanate detection in seawater could aid in maintenance of equipment in salt-water environments. Most thiocyanate that is detected natively in marine or terrestrial environments is generated biotically as a metabolite in response to cyanide in the environment. For example, a sensitive sensor for thiocyanate may have application to future NASA missions to detect life in aqueous environments within our solar system. Detection of thiocyanate would be a suggestive indicator for microbial life.

There are a number of problems typically associated with accurately identifying fish that have been caught by cyanide fishing. Currently for law enforcement to determine that a fish has been caught via cyanide fishing, they must sacrifice some sample fish for blood testing in a laboratory, or by a newer method, possibly detect thiocyanate in the water around the fish via a modified high-pressure liquid chromatography technique that is laboratory based with a detection limit of 3.2 ppb in seawater after preconcentrating the sample.

There is a need for a hand-portable chemosensor device that can detect thiocyanate in seawater directly without treatment down to under 2 ppb; use of the chemosensory electrode in a laboratory environment for cyclic voltammetry on seawater to below 1 ppb. Rapid, on-site analysis in this fashion is highly desirable and would provide increased forensic capability for law enforcement by entities such as the U.S. Fisheries and Wildlife Service. The use of electrodes in laboratory analysis extends the capability of sensitive detection significantly.

There have been some attempts in the prior art to address these needs. The most direct comparison in the literature or amongst patents is a method using polyethyleneglycol (PEG) modified optical fibers in line with HPLC separation to detect thiocyanate in seawater down with-a detection limit of 3.2 ppb (Silva, I7.I.B., et. Al.; J Environmental Monitoring, 2011, 13, 1811). Another HPLC method touted for its sensitivity in recent literature describes HPLC with ion detection, used to characterize naturally occurring thiocyanate in cow's milk in the ppm regime (Phonchai, A., et. Al.; Analytical Methods, 2016, 8, 4983). There are air quality sensors that detect volatile organic compounds (VOCs) that are hand portable and capable of detecting methyl thiocyanate at 0.1-5000 ppm (http://www.ionscience.com/products/tigerlt).

There are numerous prior art patents that are directed to a "thiocyanate chemosensor". However, the vast majority of those prior art patents have thiocyanate as a component to aid in detection of metal ions. There is a subset of patents for the detection of thiocyanate in saliva related to cigarette smoking, and HPLC methods that are patented for thiocyanate detection in food. In both cases of smoking and food, the dangerous limits for thiocyanate are on the order of ppm, rather than ppb, so the sensitivity in these methods is not comparable.

Further, the use of metalloporphyrins for ion sensing, including detection of thiocyanate are well known (Zhang, Y; Wang, H.; Yang, R. H.; Sensors, 2007, 7, 410), with the emphasis on colorimetric and/or fluorescent detection of ions is also well known in the art. In Zhang and coworkers paper, their detection limit was $6.00 \times 10^{-4}$ M (equivalent to 34.8 ppm) which is much less sensitive than the Silva HPLC/optical fiber method. In addition, halide ions (chloride Cl—, bromide Br—, iodide I—) are potential interferents for colorimetric/fluorescent detection which makes the method unsuitable for marine environments.

Despite the attempts in the prior art, there is still a need for a device, method and system that detects thiocyanate in seawater with the halide ions present; a device that is hand-portable and which offers detection limits to 1-2 ppb which at least twice as sensitive as the nearest known device in the current state of the art.

SUMMARY OF THE INVENTION

The present invention preserves the advantages of prior art devices, methods and systems for detect thiocyanate in seawater and other marine locations. In addition, it provides new advantages not found in currently available devices, methods and systems and overcomes many disadvantages of such currently available devices, methods and systems.

The invention is generally directed to the novel and unique device, method and system that detects thiocyanate in seawater with the halide ions present. The device of the present invention can be configured as a hand-portable device. The device, method and system of the present invention offers detection limits to 1-2 ppb which at least twice as sensitive as the nearest known device in the current state of the art.

Current forensic techniques in combating cyanide fishing may require destruction of animals and almost always requires treatment of samples in the laboratory environment. A method published by Silva and coworkers (Silva, L. I. B., et. Al.; J Environmental Monitoring, 2011, 13, 1811) offers the currently known best sensitivity for thiocyanate in seawater (3.2 ppb) using a chemically modified optical fiber detector in line with a high pressure liquid chromatograph (HPLC) to detect thiocyanate after separation on a column. Other methods focus on direct cyanide detection in the laboratory with seawater samples that are preconcentrated and then tested with ion selective electrodes, titration, or processing of tissue samples from selected fish for analysis.

The chemosensor of the present invention functions to detect thiocyanate without any direct treatment of the seawater beyond simple filtration to remove large particulate matter that might lead to physical occlusion. In this manner, with direct comparison to other laboratory methods, our invention offers a less labor intensive analysis with greater sensitivity to thiocyanate (<1.0 ppb). The chemosensor has also been tested as part of a hand-portable unit for on-site detection. Initial results have shown the proof of concept, but indicate a loss of sensitivity (2.0 ppb) in comparison to the laboratory method. The sensor of the present invention is insensitive to common seawater anions such as chloride, bromide, and carbonate. However, sensor of the present invention has the additional advantage that is also sensitive to nitrate ions (NO3−) in seawater at similar ppb concentrations as thiocyanate.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

FIG. 11 is a graph showing cyclic voltammetry of iron (III) tetratolylporphyrin coupled substrate initially in 20 mL of filtered seawater that is then titrated with 20 µL aliquots of a 100 ppb SCN—solution in filtered seawater.

DESCRIPTION OF THE INVENTION

Figure 1:
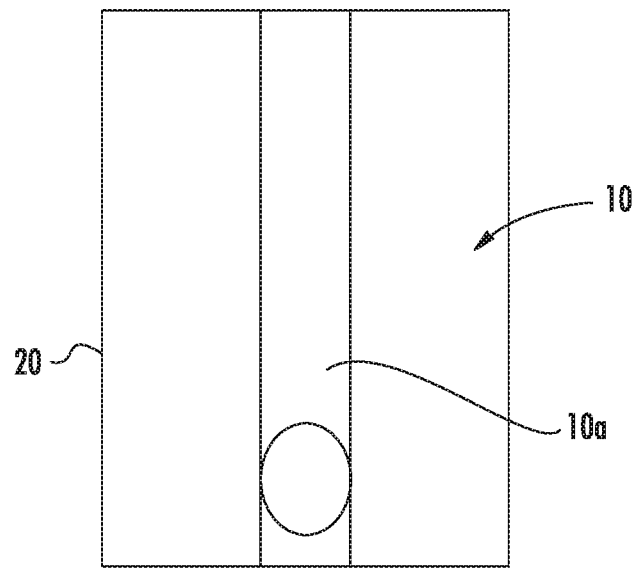
FIG. 1 is an image of the chemosensor substrate with iron (III) tetratolylporphyrin coupled to the substrate of the present invention.

The present invention provides a novel and unique device, method and system that detects thiocyanate in seawater with the halide ions present that can be provided in a hand-portable device that offers detection limits to 1-2 ppb which at least twice as sensitive as the nearest known device in the current state of the art. The sensor is also sensitive to nitrate ions (NO3−) in seawater at similar ppb concentrations as thiocyanate.

More specifically, the present invention is directed to a chemosensor 10 that detects thiocyanate and is also sensitive to nitrate ions (NO3−) in seawater at similar ppb concentrations as thiocyanate. The chemosensor 10 serves as a working electrode 12 in a potentiostat test system 100. As will be described below, when the electrodes (working electrode 12, reference electrode 14 and counter electrode 16 are immersed in the liquid 18 to be tested (e.g. seawater), the chemosensor 10 electrically reacts accordingly and, along with the other electrodes 12, 14, 16 electrically communicate with the electronics and circuitry, as will be described below in connection with FIGS. 7-10, to generate a test result.

Turning first to FIG. 1, the chemosensor 10 is first provided. A conductive glass substrate 20 is first prepared with anatase titanium dioxide which is then silanated and then metalloporphyrin moiety is coupled chemically to the electrode 12. This architecture allows for both photometric and electrochemical detection of thiocyanate in seawater 18 as thiocyanate ions coordinate to the metal centers. Preparation of the chemosensor materials are shown below.

Scheme 1. Synthesis of tetratolylporphyrin (TTP).

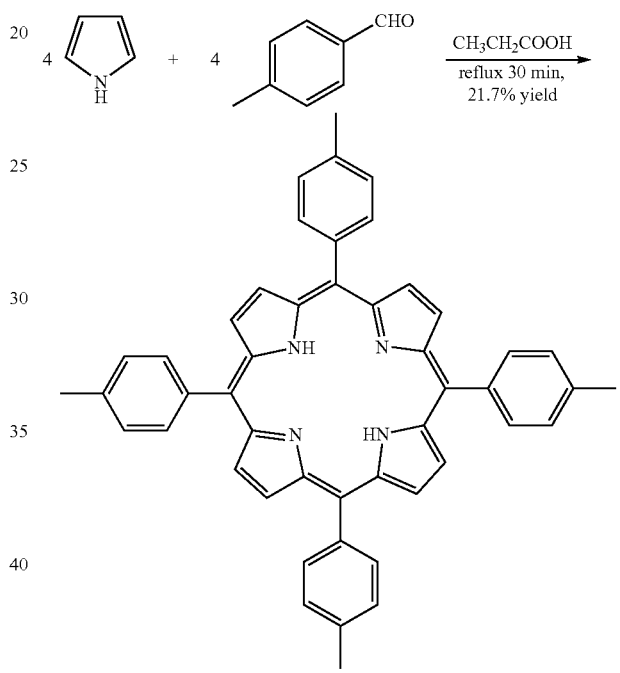

Porphyrins are synthesized in one step via the Adler synthesis, for example, in good yield, as seen in Scheme 1, above. Tetratolylporphyrins (TTPs) are then metallated by refluxing with a metal chloride solution in dimethylformamide for 30 minutes. Isolated metal-TTP was then brominated with n-bromosuccinamide to give bromomethyl groups in the para position of each meso-phenyl moiety. These materials are then suitable for coupling to prepared fluorine-doped tin oxide (FTO) substrates, as in Scheme 2 below.

Scheme 2. Preparation of the transmissive electrode chemosensor.

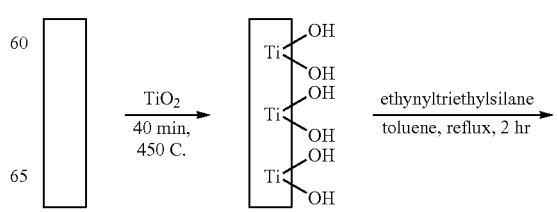

-continued

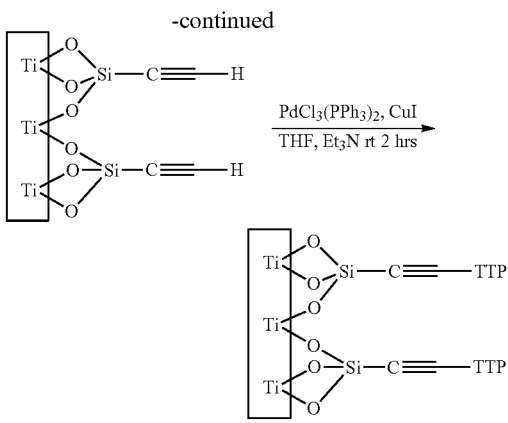

FTO slides cut to 25 mm by 20 mm area have a commercially prepared TiO2 paste coated as a thin strip layer onto the FTO by the doctor blading method, and TiO2 is annealed into a hydroxylated layer at 450° C. for 40 minutes. The resulting TiO2 is silanated with ethynyltriethylsilane in toluene reflux for two hours. This results in a terminal acetylene group that is attached to the metal-TTP complex via Sonogashira coupling, yielding a conjugated linkage from the complex to the transparent conductive substrate 20. As a result, the chemosensor 10 of the present invention provides a substrate 20 with iron (III) tetratolylporphyrin coupled thereto. This chemosensor 10 generates electrical potential depending on the level of thiocyanate present in the sample under test and, thereby, serves as a working electrode 12 in a potentiostat test system, as described below.

Figure 3:
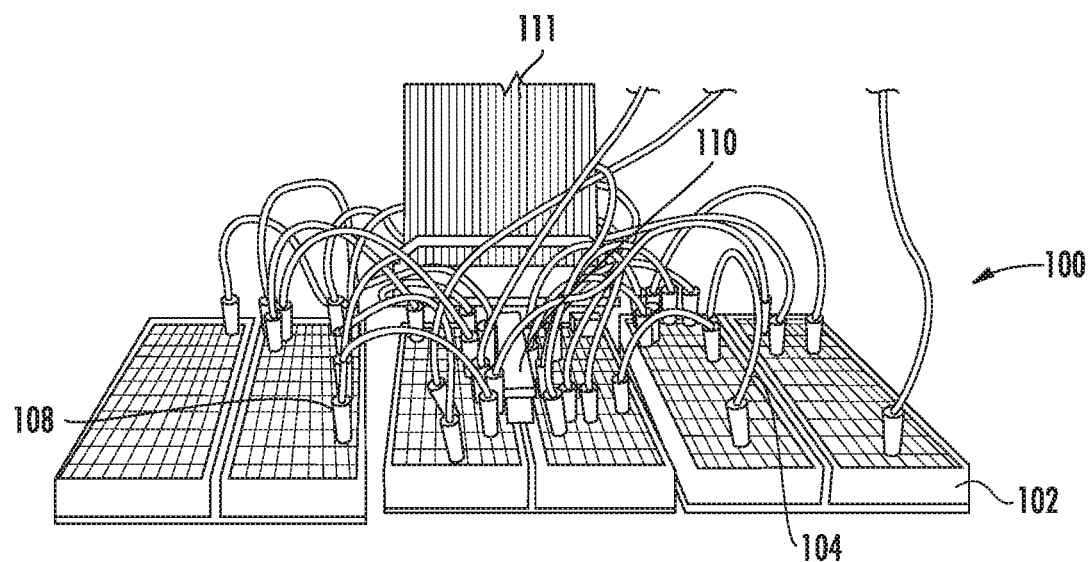
FIG. 3 shows a prototype of the test device set up on a breadboards.

Once the chemosensor 10 has been prepared, it is configured and arranged into a data processing test device 100, as in FIG. 3, so that it may be used to physically interface with and test a liquid sample 18, such as seawater. This is carried out by the use of electrodes 12, 14 and 16, interconnected to the chemosensor 10, which are in turn connected to a data processing test device 100.

First, a number of lead wires are used as electrodes to electrically interconnect the chemosensor 10. For CV scans, the chemosensor 10 itself is the working electrode 12. As seen in FIG. 1, the chemically modified electrode is the center strip 10a, which is the bladed TiO2 layer, modified by silanation and porphyrin coupling, as described herein. The entirety of the side of the glass 20 that has the strip 10a deposited thereon is coated with an electrically conductive fluorine-doped tin oxide (FTO) layer. The working electrode is clipped to 10, and then the entirety of the center strip 10a is immersed in the test solution.

All three electrodes are immersed in the test solution. Electrode 16 is the reference electrode, which is preferably made of silver/silver chloride (Ag/AgCl). Electrode 12 is connected to platinum wire (Pt) and serves as the counter electrode. Electrode 14 is connected to the chemically modified conducting glass electrode 10, which serves as the working electrode.

The chemosensor 10 electrodes are preferably prepared with a variety of metal centers in the porphyrin, for example, including iron (III), zinc (II), ruthenium (III), cobalt (II) and plan to include copper (II), manganese (II), and other metal centers in order to vary sensitivity to thiocyanate and ensure specificity of response to thiocyanate ions in the presence of potential interferents. Chemosensor electrode architecture can vary the shape of the electrode (conductive glass rod, conductive glass disc) for immersion or construction of conductive glass sample chambers with the chemosensor material in place.

Figure 2:
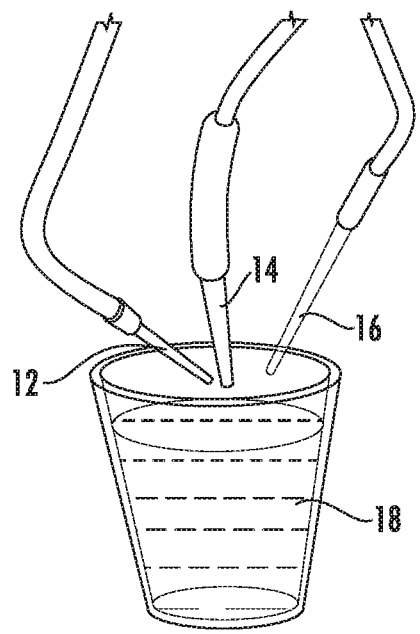
FIG. 2 shows the chemosensor of FIG. 1 immersed in seawater with electrodes installed.
Figure 5:
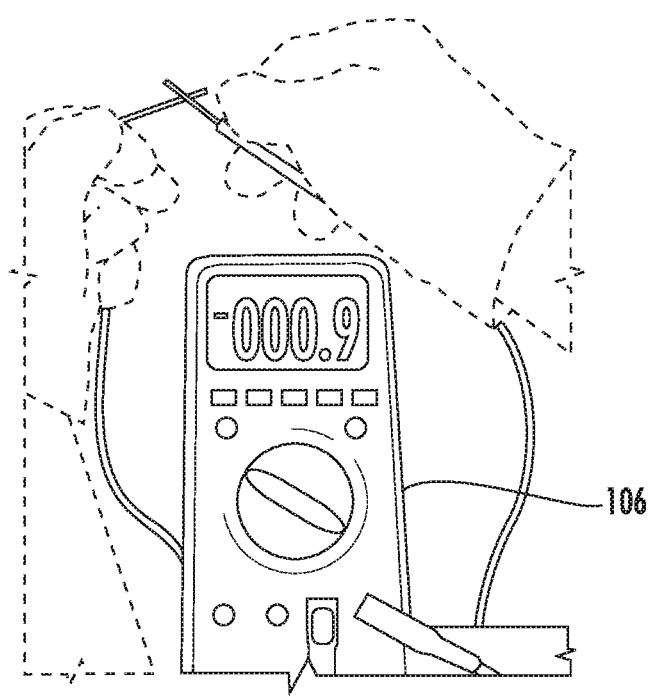
FIG. 5 shows initial reading from the multimeter for current for the iron (III) tetratolylporphyrin electrode in filtered seawater.
Figure 6:
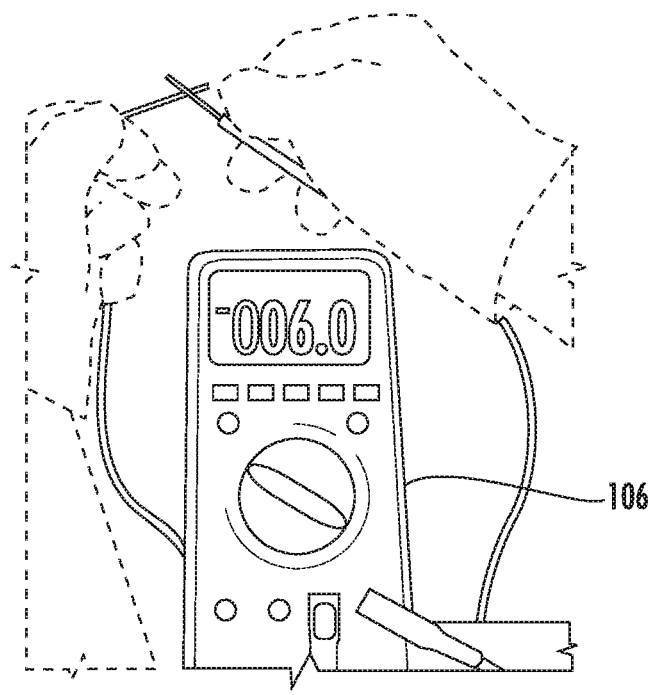
FIG. 6 shows a reading for the same electrode/device set up with 4 ppb thiocyanate ion in seawater.

These chemosensor electrodes 12 are preferably used in conjunction with a potentiostat to perform cyclic voltammetry (CV) on seawater samples 18. For example, FIG. 2 shows the immersion of the electrodes 12, 14 and 16 in a seawater sample 18 for test. As shown in FIGS. 3-6, the electrodes 12, 14 and 16 of the device are electrically interconnected to an electronic test device 100. The actual test device 100 may be configured in any form, but it is preferably in a handheld portable configuration. The device 100 and its components are representationally shown in FIG. 3 where the test device 100 is shown as circuit breadboards 102 electrically connected to various leads 104 and electrodes 12, 14 and 16 and arranged for reading sensed data initially with a multimeter 106, as shown in FIGS. 5 and 6. More specifically, FIG. 3 shows the device 100 with its circuit components, generally referenced as 108, of the present invention on representative breadboards 102 and further employing a compact computing device 110, such as a Raspberry Pi™, for example, which is connected to the breadboards 102 by ribbon cable 111. The use of such a data processing computing device 110 like a Raspberry Pi processor helps interpret the current produced at a chemosensor electrode 12 at a fixed voltage to return information on the amount of thiocyanate present in the solution. It should be understood that the used of breadboards 102, and the like, are for design purposes only and that it is intended that device 100 would be miniaturized and configured to be a much smaller device by use of microprocessors, other semiconductor circuit devices, and the like.

Figure 4:
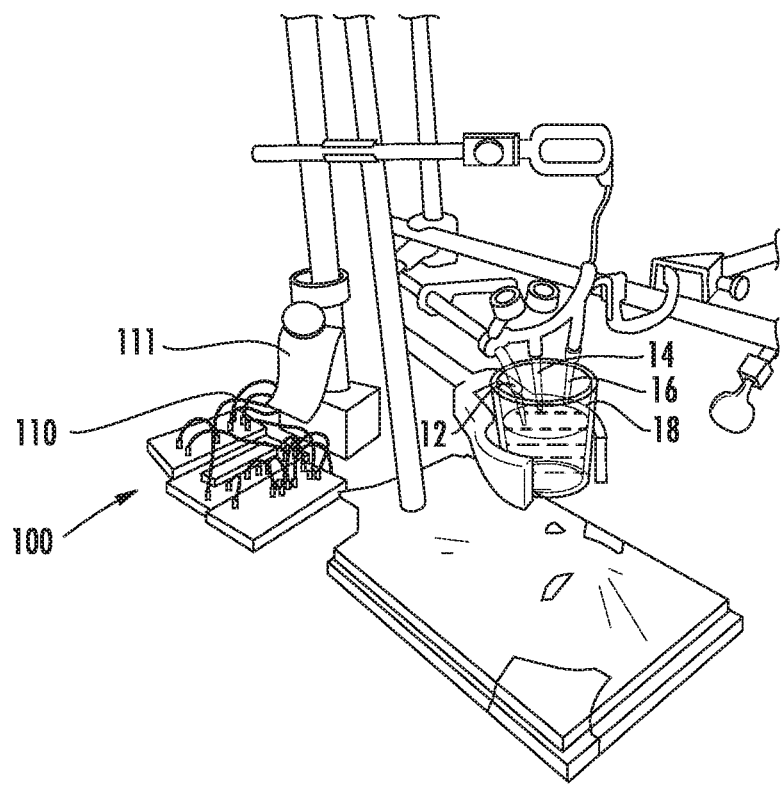
FIG. 4 shows the same sample circuit connected to the chemosensor electrode setup.

FIG. 4 shows the same sample circuit 100 connected to the chemosensor electrode setup; FIG. 5 shows initial reading from the multimeter 106 for current for the iron (III) tetratolylporphyrin electrode in filtered seawater 18; and FIG. 6 shows a reading for the same electrode/device set up with 4 ppb thiocyanate ion in seawater 18.

Test data in the laboratory is preferably acquired using a Princeton Applied Research VersaSTAT 4 potentiostat. Thus, the chemosensor 10 must be incorporated into electronics and circuitry so the testing may be carried out and controlled and, preferably made suitable for providing the sensing technology methodology as a hand-portable device which is a critical advancement in forensic capacity for law enforcement with respect to cyanide fishing.

Figure 7:
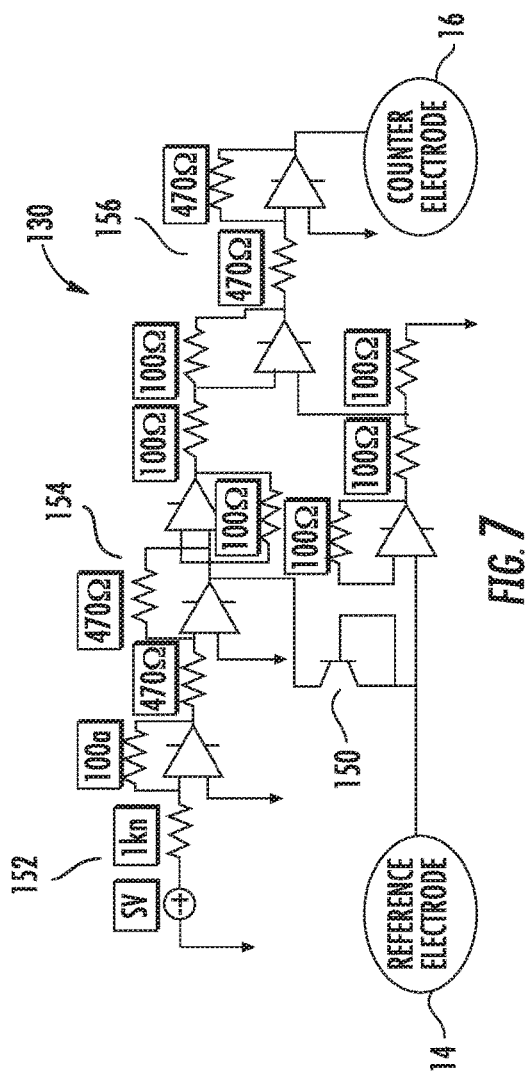
FIG. 7 is a circuit diagram for the reference electrode and counter electrode of the test device in accordance with the present invention.
Figure 8:
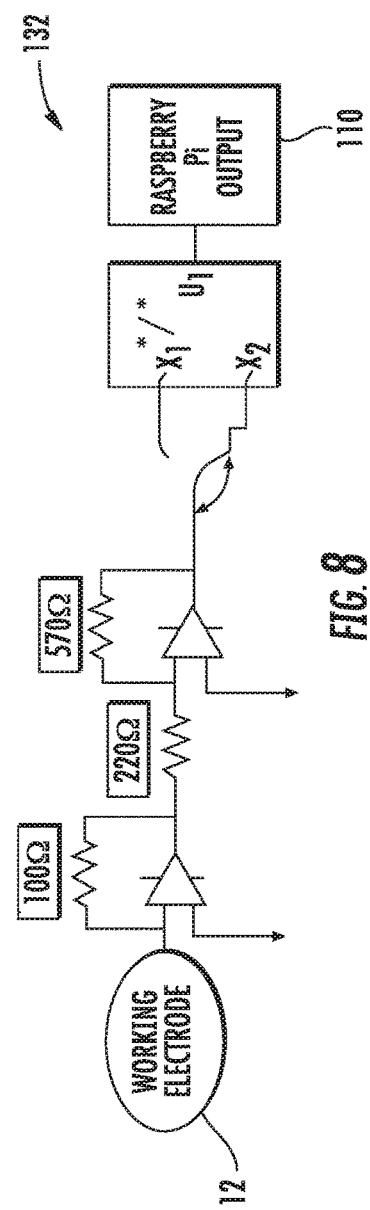
FIG. 8 is a circuit diagram for the working electrode of the test device in accordance with the present invention.

To carry out the processing of the current data received by the electrodes 12, 14 and 16 into the device 100 and for measurement via a multimeter 106, it is preferred that the device 100 include various data processing circuitry to parse and output the test results for the portable reproduction of cyclic voltammetry data. FIGS. 7 and 8 show a first embodiment of circuit diagram for the device 100 of the present invention for the for portable reproduction of cyclic voltammetry data while FIGS. 9 and 10 shows an alternative embodiment of the circuit diagram for the device 100 of the present invention for the for portable reproduction of cyclic voltammetry data.

In FIG. 7, a circuit diagram 130 for processing of data for reference electrode 14 and counter electrode 16 is shown. In FIG. 8, a circuit diagram 132 for the processing of data for working electrode 12. In FIG. 9, an alternative embodiment of the processing circuitry 140 for processing data for reference electrode 14 and counter electrode 16 is shown. FIG. 10 shows an alternative circuit diagram 142 for the processing of data for working electrode 12.

Figure 9:
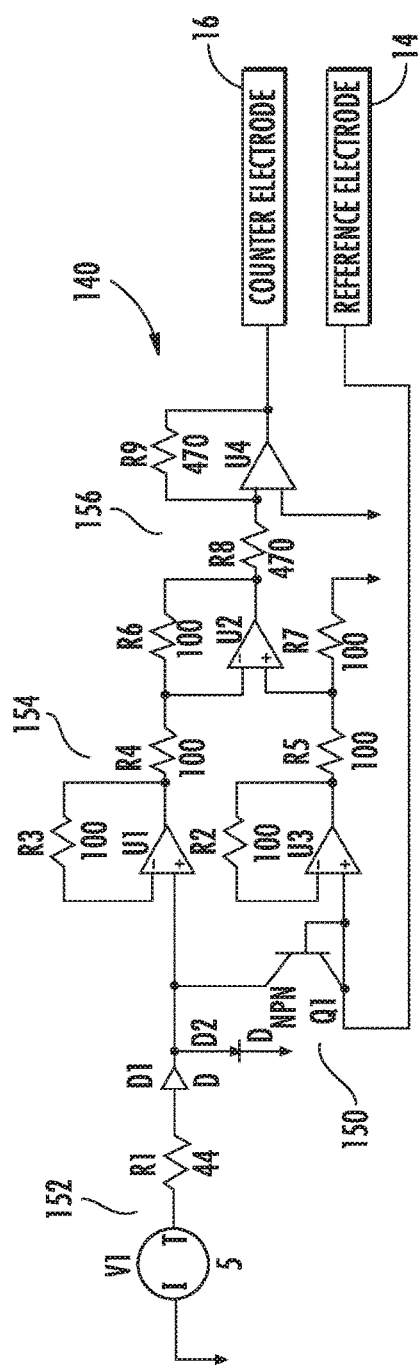
FIG. 9 is an alternative embodiment of a circuit diagram for the reference electrode and counter electrode of the test device in accordance with the present invention.

Referring to both FIGS. 7 and 9, both embodiments generally show the reference electrode 14 providing current to a NPN transistor 150, which is used to inhibit a large resistance from over-taking the circuit. This NPN transistor 150 allows voltage and current to flow freely through both sides of the circuit 130, 140. The resistor diode combination 152 reduces the 5V source to a 0.8V input that is most suitable for the circuit of the present invention. The operational amplifiers 154 are oriented in a negative feedback loop with the 0.8V input and reference electrode 14 so as to correct for any voltage drops. The output section 156 of the circuitry transforms the positive output voltage of the circuit into a negative one that can be used effectively in the working area.

Figure 10:
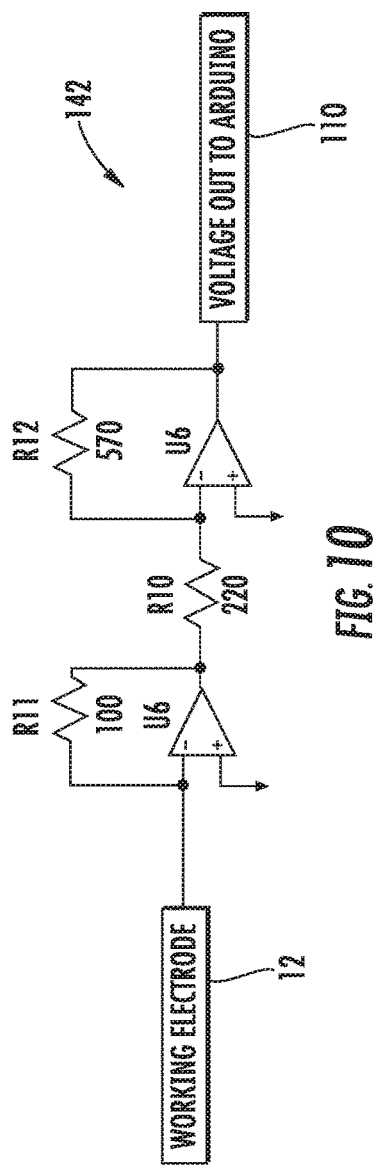
FIG. 10 is an alternative embodiment of a circuit diagram for the working electrode of the test device in accordance with the present invention.

Referring now to the working electrode circuits 132, 142 of the embodiments shown in FIGS. 8 and 10, this circuit coverts the current produced by the working area into a voltage and then amplifies it by 2.5. This output is then provided to a computing device 110, such as a Raspberry Pi or Arduino, for further data processing, including logging and display of the test results. It should be noted that these circuits 130, 132, 140, 142 are just examples of how the sensed currents by the electrodes 12, 14, 16 employed in the invention may be processed for further use in accordance with the present invention.

The above device and system is preferably configured into a portable device with a user interface (not shown) where the testing circuits are battery powered to facilitate portability. Portable, battery powered, AC powered, DC powered, or any other power configuration is also possible and considered within the scope of the present invention.

FIG. 11 shows some sample test results using the chemosensor 10 and device 110, 110 of the present invention. Initial testing of the electrodes prepared with iron (III) tetratolylporphyrin were completed by titrating the electrode in filtered (1 micron mesh) seawater from Mt. Hope bay with a separate portion of the same seawater adulterated with sodium thiocyanate or potassium thiocyanate to fixed concentrations. More specifically, FIG. 11 shows a graph of cyclic voltammetry of iron (III) tetratolylporphyrin coupled substrate initially in 20 mL of filtered seawater that is then titrated with 20 μL aliquots of a 100 ppb SCN—solution in filtered seawater. Each 20 μL addition corresponds to approximately 0.10 ppb thiocyanate present in solution. FIG. 11 shows results for 20 mL seawater at 200, 20 uL SCN—at 202, 40 uL SCN—at 204, 60 uL SCN—at 206, 80 uL SCN—at 208 and 100 uL SCN—at 210.

As a result, the novel and unique device, method and system that detects thiocyanate in seawater with the halide ions present that can be provided optimally in a hand-portable device that offers detection limits to 1-2 ppb which at least twice as sensitive as the nearest known device in the current state of the art.

It would be appreciated by those skilled in the art that various changes and modifications can be made to the illustrated embodiments without departing from the spirit of the present invention. All such modifications and changes are intended to be covered by the appended claims.

What is claimed is:

1. A chemosensor, comprising:
   a conductive glass substrate with anatase titanium dioxide which is deposited and cured thereon then silanated;
   at least one electrode connected thereto; and
   a metalloporphyrin moiety chemically coupled to the at least one electrode;
   wherein the chemosensor is configured and arranged to both photometrically and electrochemically detect thiocyanate in seawater when thiocyante ions in seawater coordinate to a metal center of the metalloporphyrin moiety.

2. The chemosensor of claim 1, wherein the at least one electrode is a counter electrode, a reference electrode and a working electrode.

3. A method for detecting thiocyanate in a liquid, comprising the steps of:
   providing a conductive glass substrate with anatase titanium dioxide which is deposited and cured on the conductive glass substrate;
   silanating the anatase titanium dioxide;
   chemically coupling a metalloporphyrin moiety to at least one electrode, wherein the at least one electrode is interconnected to the conductive glass substrate;
   contacting the liquid with the conductive glass substrate interconnected with the least one electrode; and
   measuring a concentration of thiocyanate in the liquid by both photometric detection and electrochemical detection of thiocyanate in the liquid when thiocyanate ions in the liquid coordinate to a metal center of the metalloporphyrin moiety,
   wherein the liquid is seawater.

4. The method of claim 3, wherein the at least one electrode is a counter electrode, a reference electrode and a working electrode.

* * * * *